US 6,719,960 B1

(12) United States Patent
Hills et al.

(10) Patent No.: US 6,719,960 B1
(45) Date of Patent: Apr. 13, 2004

(54) USE OF PHOSPHOLIPIDS FOR THE MANUFACTURE OF A MEDICAMENT FOR THE PREVENTION OF ADHESIONS

(75) Inventors: Brian Andrew Hills, Cleveland (AU); Derek Alan Woodcock, Berkhampstead (GB)

(73) Assignee: Britannia Pharmaceuticals Ltd., Redhill Surrey (GB)

( * ) Notice: Subject to any disclaimer, the term of this patent is extended or adjusted under 35 U.S.C. 154(b) by 0 days.

(21) Appl. No.: 09/582,286

(22) PCT Filed: Nov. 26, 1998

(86) PCT No.: PCT/GB98/03540

§ 371 (c)(1),
(2), (4) Date: Aug. 10, 2000

(87) PCT Pub. No.: WO99/51244

PCT Pub. Date: Oct. 14, 1999

(30) Foreign Application Priority Data

Apr. 3, 1998 (GB) .............................. 9807298

(51) Int. Cl.[7] .............................. A61K 9/04; A61K 9/00; A61K 9/127; A61K 9/14
(52) U.S. Cl. .................. 424/46; 424/400; 424/489; 424/450; 514/951
(58) Field of Search ................ 424/489, 400, 424/450, 423, 46; 514/78, 947, 951

(56) References Cited

U.S. PATENT DOCUMENTS

| 4,828,844 A | * | 5/1989 | Rontgen-Odenthal et al. ... 424/489 |
| 5,438,044 A | * | 8/1995 | Losch et al. .................. 514/78 |

FOREIGN PATENT DOCUMENTS

| EP | 0528034 | 2/1993 |
| JP | 58164513 | * 9/1983 |
| WO | WO87/07502 | * 12/1987 |
| WO | WO9112026 | 8/1991 |
| WO | WO 91/12026 | * 8/1991 |
| WO | WO9853800 | 12/1998 |

OTHER PUBLICATIONS

Snoj et al., "Effect of . . . in the rat". Br. J. Surg. 79:427–429, 1992.
Ar Rajab et al., "Phosphatidylcholine . . . in the rat", J. Surg. Res. 50:212–215, 1991.

* cited by examiner

Primary Examiner—Thurman K. Page
Assistant Examiner—Sharmila S Gollamudi
(74) Attorney, Agent, or Firm—GrayCary LLP; Dean H. Nakamura

(57) ABSTRACT

A medicament is disclosed for reducing the risk of cross-healing ("adhesions") after surgery. The medicament is a dry powder comprising a surface active phospholipid which is capable of binding to mesothical membranes, and a spreading agent. The medicament is applied as a dry powder to the surgical wound site.

9 Claims, 2 Drawing Sheets

Figure 1:
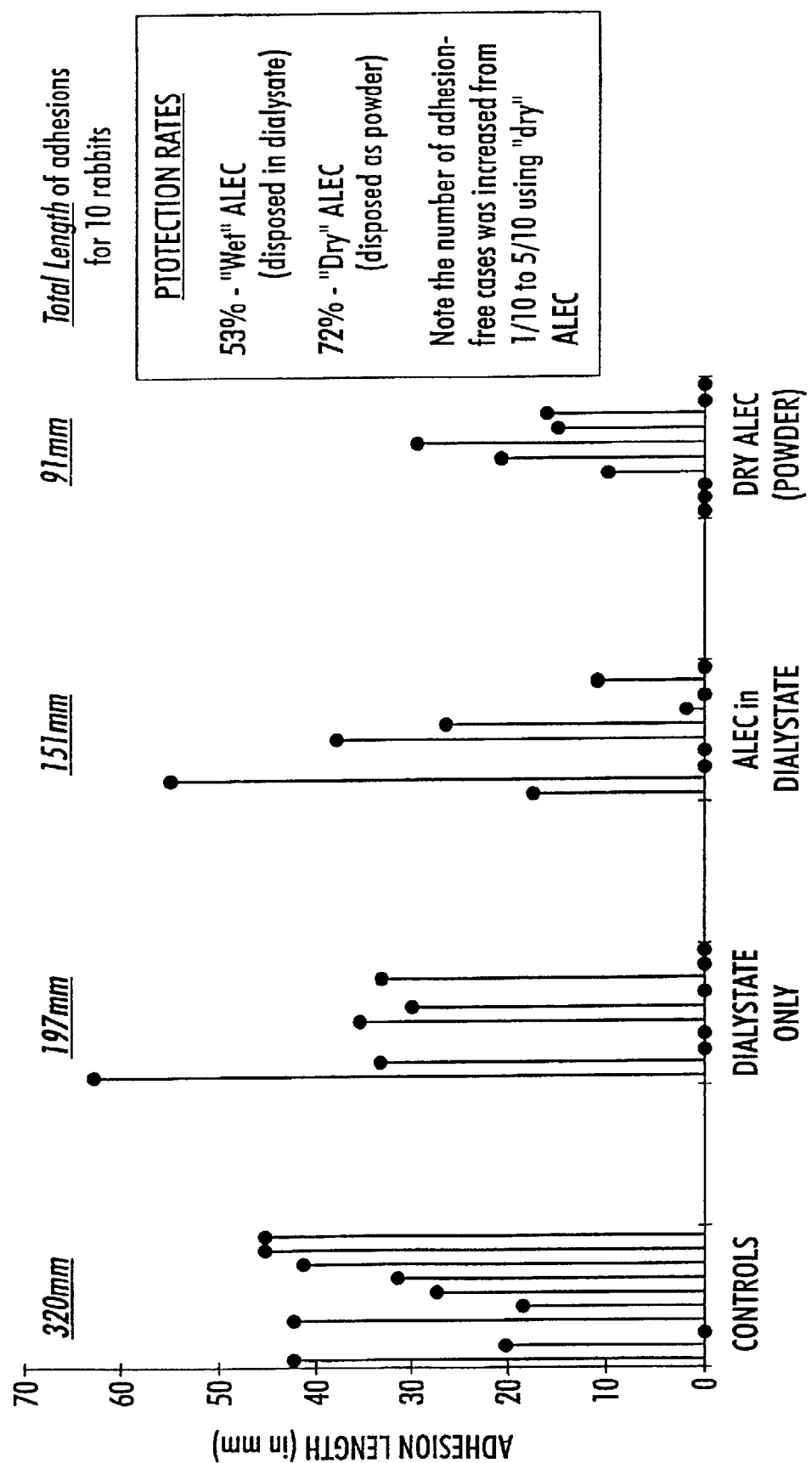

USE OF PHOSPHOLIPIDS FOR THE MANUFACTURE OF A MEDICAMENT FOR THE PREVENTION OF ADHESIONS

This invention relates to medicaments for and methods of reducing the probability of surgical adhesions.

Following surgery, membranes which have been severed may 'cross-heal'. For example the abdominal wall can heal with the peritoneum and adhere to it. This is known as an adhesion. A very serious complication of adhesions inside the peritoneum is intestinal obstruction. Unless corrected surgically this can rapidly be fatal. It has been estimated that in the US in 1988 the cost of correcting lower abdominal pelvic adhesions was of the order of US$ 1180 million (AH De Cherney and GS diZeregram Surgical Clinics of North America 77(3), 671). Attempts have been made to reduce adhesions by providing physical barriers such as sheets of hyaluronic acid and carboxymethylcellulose. While providing an initial barrier the sheets degrade.

It has now been unexpectedly found that natural occurring surface active phospholipids and enantiomers thereof can substantially reduce the likelihood of adhesions forming.

According to the invention there is provided a method of reducing the probability of surgical adhesion comprising administering SAPL to mesothical membranes during surgery.

According to the invention there is provided the use of a SAPL in the manufacture of a medicament for use in reducing the probability of surgical adhesions following surgery.

Embodiments of the invention will be described by way of non-limiting example by reference to the Figure which shows the length of adhesion formed under various conditions.

A physical or chemical binding of the surfictant to the membrane is highly desirable. Examples of suitable phospholipids include diacyl phosphatidyl cholines (DAPC's) such as dipalmitoyl phosphatidyl choline (DPPC), dioleyl phosphatidyl choline (DOPC) and distearyl phosphatidyl choline (DSPC). It is also preferred to include a spreading agent in the composition to assist the DPPC or analogous compound rapidly to form a thin film over the surface of the membrane. A number of agents are capable of acting in this way including other phospholipids, such as phosphatidylglycerols (PG); phosphatidylethanolamines (PE); phosphatidylserines (PS) and phosphatidylinositols (PI). Another useful spreading agent is cholesteryl palmitate (CP). We prefer to use dipalmitoyl phosphatidyl choline (DPPC) and unsaturated phosphatidyl glycerol (PG) either alone or in combination. A mixture comprising DPPC 70 wt % and PG 30 wt % can be used. This material is commercially available as ALEC™ from Britaia Pharmaceutical Limited. ALEC is known for use in treating respiratory distress syndrome see for example British Medical Journal 294 (1984) 991–996.

A widely accepted theory on the mechanism of action of ALEC in the lungs of neonates is that it functions principally by lowering surface tension Since there is no air-water interface in the normal peritoneal cavity one would not expect ALEC and other SAPL's to be effective in preventing the formation of or reduction the probability of forming adhesions. It has however been experimentally found that SAPL's do, in fact reduce the frequency of adhesion formation as will become apparent from the experimental data set forth below.

40 rabbits were taken. A surgical opening was made in the peritoneum Opposing peritoneal surfaces were subjected to a sterilised 50 mm abrasion. In 10 cases the opening was simply closed. In a further 10 cases the abrasion was perfused with dialysate prior to closure. In a still further 10 cases the abrasion was perfused with a suspension of ALEC in dialysate and the opening closed. In a final 10 cases powdered ALEC was blown into the abrasion prior to closure. Following healing the peritoneum was reopened and the presence of adhesions noted. Where adhesions were noted their length was measured. The results are shown in Table 1.

TABLE 1

|  | Control | Dialysate | ALEC & Dialysate | ALEC |
|---|---|---|---|---|
| Number of adhesion free cases | 1 | 5 | 4 | 5 |
| Total length of adhesion (mm) | 320 | 197 | 151 | 91 |
| Reduction in adhesion length relative to control | — | 38% | 53% | 72% |
| Mean Adhesive Length (mm) | 32 | 19.7 | 15.1 | 9.1 |
| Standard Deviation | 5 | 10.5 | 9 | 5 |

One can say therefore with a high degree of confidence (even with a very limited number of samples) that ALEC powder markedly reduces both the likelihood of adhesion formation and the length of the adhesions which do form. There is also evidence that a suspension of ALEC is more effective than either no treatment or treatment with dialysate.

Preferably the SAPL is used in the form of a dry powder aerial dispersion.

Phosphatidyl glycerol (PG) is believed to be capable of binding to the surface of the animal tissue and is, therefore, a preferred component of the SAPL. Dipalmitoyl phosphatidyl choline (DPPC) may function also in this way and is also a preferred compound of the SAPL. PG has a further important function in medicaments employed in the present invention which is its ability to cause the DPPC to form a dry powder. The particle size of such powders is not critical and the controlling factor is that the size is preferably such that medicament can be readily instilled into the surgical site. Generally, the particle size is within the range of 0.5 to 100 $\mu$M. Particles which are more readily conveyed in a gas stream have a particle size of from 0.5 to 20 $\mu$m, preferably 0.5 to 10 $\mu$m and more preferably 0.5 to 2 $\mu$m. Finely-divided dry powders of this kind are believed to be absorbed very rapidly onto the surfaces of mesothical membranes, i.e. bound to the epithelium. Preferably, the SAPL compositions employed in the present invention are blends of dipalmitoyl phosphatidyl choline (DPPC) and PG, although as indicated above, other phospholipids may be employed.

The medicament should generally be essentially free from animal protein in order to avoid the danger of patient sensitivity to animal proteins. Also, animal proteins may become adhesive and, for this reason, should preferably be excluded from the compositions.

DPPC is commercially available from Sigma Chemical Co. Ltd. or can be prepared synthetically by the use of acyl chlorides using the method of Baer & Bachrea—Can. J. Of Biochem. Physiol 1959; 37, page 953 and is available commercially from Sigma (London) Ltd. The PG may be prepared from egg phosphatidyl choline by the methods of Comfurions et al and Dawson, Biochem. Biophys Acta 1977; 488; pages 36–42 and Biochem J. 1947; 192; pages 205–210.

The medicaments employed in the present invention are generally finely-divided dry powders having a particle size distribution which is small enough to be introduced into the surgical site in a gas stream from a dispersion device. The material available commercially as 'Alec' has a particle size distribution such that a major proportion is between 0.5 and 2 µm with a median particle diameter of about 1.2 µm. However, as mentioned above, larger particle size powders can be satisfactorily used in accordance with the invention. The medicament of the present invention may be introduced into the surgical site through a cannula, e.g. connected to a syringe.

However, we prefer to employ a dispersion device which utilises a propellant. These may employ a propellant such as a halocarbon to form a gas stream and may include a tapered discharge nozzle, baffle or venturi to accelerate particles through a discharge nozzle. Suitable halocarbons include hydrofluorocarbons, hydro-fluorochlorocarbons and fluorochlorocarbons having a low boiling point, such as those marketed by DuPont under the trade marks "Freon" and "SUVA". Pharmaceutically acceptable hydrofluoroalkanes are available as HFA-134a and 227.

Figure 2:
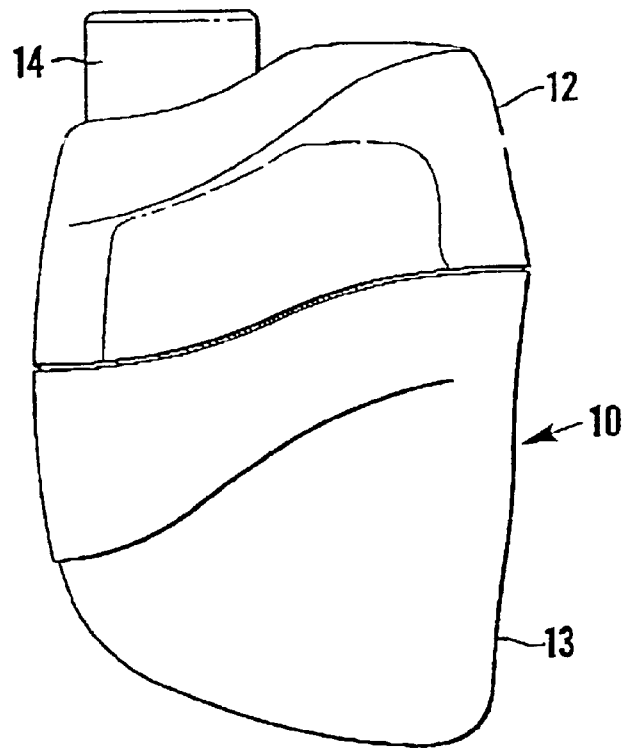
Figure 3:
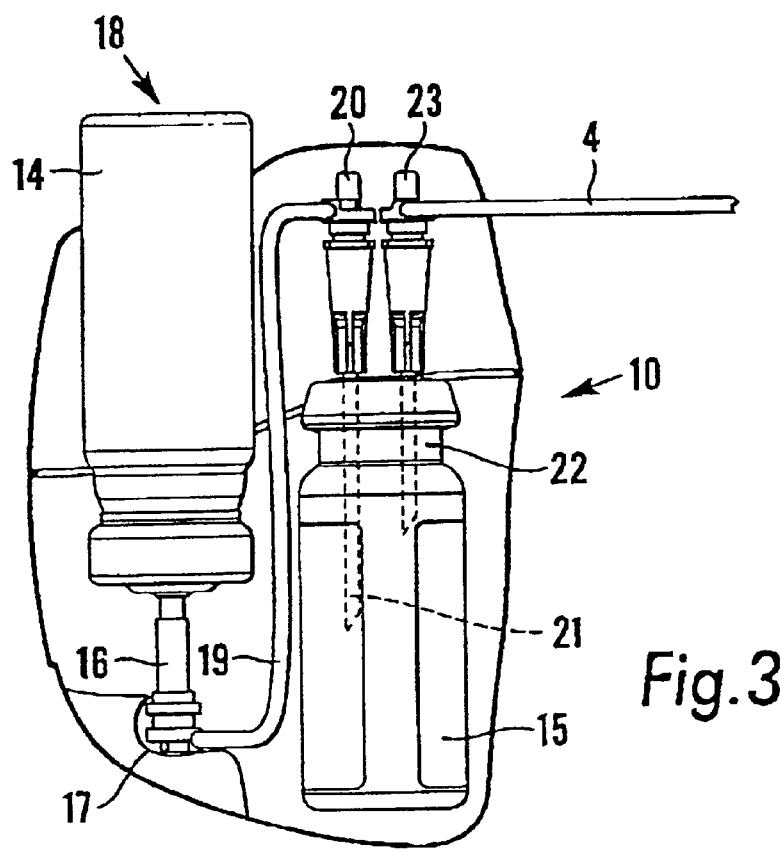

One suitable design of dispensing device for administering the powdered material to a surgical site is shown in FIGS. 2 and 3 in which:

FIG. 2 is a side elevation of the dispenser; and
FIG. 3 is a similar view, but shows its interior.

Referring to FIGS. 2 and 3, a casing (10) is formed from two plastic mouldings (12 & 13) which snap together to form a container for a pressurised canister (14) and a vial (15). Canister (14) contains a low boiling liquid, preferably a hydrofluorocarbon such as HFA-134a or HFC-227, under sufficient pressure to maintain the propellant liquid at normal room temperature. Vial (15) contains the powdered medicament, such as "Alec". Canister (14) has a release valve (16) which is received in a recess (17) so that finger pressure on the inverted end (18) of the canister will cause propellant to be released into a tube (19). Tube (19) is typically a hard plastics, e.g. pvc or polypropylene, tube of about 2–3 mm outside diameter and about 0.5 to 2 mm inside diameter. Tube (19) connects valve (16) with a fitting (20) and thence to a tube or needle (21) which extends into the vial (15). Vial (15) may be closed with a rubber seal which is penetrated by the tube or needle (21) and self-seals around the tube or needle. A second needle or tube (22) extends part way into the vial through the rubber seal in the neck of the vial and connects with a fitting (23). Fitting (23) discharges into a catheter (4) from which the powder can be directed to the desired area of the surgical site. The advantage of the dispenser shown in FIGS. 2 and 3 is that it can be operated 'one-handed' while the doctor or nurse ensures that the catheter is correctly positioned to distribute powder into the surgical site. A catheter may not be necessary. The powder may simply be sprayed onto the area of the surgical wound.

In general, the DPPC and PG may be present in a weight ratio of from 9:1 to 1:9. Compositions employed in current formulations have been in the weight ratio of from about 6:4 to 8:2.

It is desirable that the SAPL (or its active component) should not break down rapidly in the environment of the surgical wound. One of the factors which will reduce the life of a release lining or coating will be the presence of enzymes capable of digesting DPPC and/or PG. Such enzymes only attack the laevo rotatory (L) form, which constitutes the naturally occurring form. Therefore, the anti-adhesion medicament should preferably contain the dextro rotatory (D form) or at least comprise a racemic mixture which is obtained by synthetic preparation routes. This also applies to the other SAPL/s mentioned above.

As an alternative to use as a powder dispersion, the medicament may be used as a dispersion in an inert liquid, for example, in sterile saline, preferably isotonic saline, which is approximately 0.9% aqueous sodium chloride.

The SAPL may comprise phosphatidyl glycerol (PG) either alone or in admixture with other components. PG has a useful additional function of forming very finely divided dispersions.

The SAPL may comprise dipalmitoyl phosphatidyl choline (DPPC) either alone or in admixture with other components such as PG.

In preferred embodiments the medicament is essentially free of animal protein to avoid patient sensitivity and also to aid the formation of finely divided particle.

When PG and DPPC are co-precipitated from a common solvent a fine powder is formed. At a weight ratio DPPC: PG of about 7:3 the mixture spreads rapidly at body temperature.

In general the weight ratio DPPC:PG lies in the range 9:1 to 1:9 preferably 6:4 to 8:2.

It may be advantageous to include other active substances into the medicament, such as anti-fungal or anti-bacterial agents.

What is claimed is:

1. A method for reducing the risk of adhesions following surgery on a human or animal patient, wherein a surface active phospholipid (SAPL) composition in the form of a dry powder comprising dipalmitoyl phosphatidyl choline (DPPC) and phosphatidyl glycerol (PG) in a DPPC:PG weight ratio of about 7:3 is delivered as a dry powder aerial dispersion to the site of a surgical procedure, and wherein said delivered dry powder is more effective at reducing adhesions then when said SAPL is delivered as a liquid.

2. The method of claim 1, wherein said SAPL composition is delivered by a propellant as a dry powder aerial dispersion.

3. The method of claim 2, wherein said propellant is a hydrofluoroalkane.

4. The method of claim 1, wherein said SAPL composition has a particle size of from about 0.5 µm to about 20 µm.

5. The method of claim 1, wherein said dry powder aerial dispersion is generated by a dispersion device for said SAPL composition, said dispersion device utilizing a propellant to disperse said SAPL dry powder in a gas stream to spray said powder to said surgical site.

6. The method of claim 4, wherein said particle size is from about 0.5 µm to about 10 µm.

7. The method of claim 6, wherein said particle size is from about 0.5 µm to about 2 µm.

8. The method of claim 1, wherein said dry powder composition is delivered with a cannula or a catheter.

9. The method of claim 1, wherein said composition further comprises an antifungal agent, an antibacterial agent or both.

* * * * *